(12) United States Patent
Neveling et al.

(10) Patent No.: US 11,833,179 B2
(45) Date of Patent: Dec. 5, 2023

(54) PROBIOTIC COMPOSITION

(71) Applicant: Stellenbosch University, Western Cape Province (CA)

(72) Inventors: Deon Pieter Neveling, Western Cape Province (ZA); Leon Milner Theodore Dicks, Western Cape Province (ZA)

(73) Assignee: Stellenbosch University, Western Cape Province (ZA)

( * ) Notice: Subject to any disclaimer, the term of this patent is extended or adjusted under 35 U.S.C. 154(b) by 70 days.

(21) Appl. No.: 16/755,801

(22) PCT Filed: Oct. 15, 2018

(86) PCT No.: PCT/IB2018/057976
§ 371 (c)(1),
(2) Date: Apr. 13, 2020

(87) PCT Pub. No.: WO2019/073460
PCT Pub. Date: Apr. 18, 2019

(65) Prior Publication Data
US 2021/0393709 A1   Dec. 23, 2021

(30) Foreign Application Priority Data
Oct. 13, 2017 (ZA) ................................. 201706932

(51) Int. Cl.
| | | |
|---|---|---|
| *A61K 35/747* | (2015.01) | |
| *A23K 50/75* | (2016.01) | |
| *A23K 10/18* | (2016.01) | |
| *A61P 31/04* | (2006.01) | |
| *A61K 9/00* | (2006.01) | |
| *A61K 35/742* | (2015.01) | |
| *A61K 35/744* | (2015.01) | |

(52) U.S. Cl.
CPC ............ *A61K 35/747* (2013.01); *A23K 10/18* (2016.05); *A23K 50/75* (2016.05); *A61K 9/0056* (2013.01); *A61K 35/742* (2013.01); *A61K 35/744* (2013.01); *A61P 31/04* (2018.01); *A23Y 2220/43* (2013.01); *A23Y 2220/79* (2013.01)

(58) Field of Classification Search
CPC ............ A23Y 2220/79; A23Y 2220/43; A23Y 2220/00; A61K 35/747; A23K 50/75
See application file for complete search history.

(56) References Cited

U.S. PATENT DOCUMENTS

| | | |
|---|---|---|
| 2013/0045185 A1 | 2/2013 | Davis et al. |
| 2013/0330307 A1 | 12/2013 | Millan |
| 2017/0224745 A1 | 8/2017 | Dart |

FOREIGN PATENT DOCUMENTS

CN         106720940 A    5/2017

OTHER PUBLICATIONS

Saint-Cyr, et al., "Recent Advances in Screening of Anti-Campylobacter Activity in Probiotics for Use in Poultry", Frontiers in Microbiology, vol. 7, Article 553, pp. 1-22. (Year: 2016).*
Neil-Mckinney et al., "Production of Organic Acids by Probiotic Lactobacilli Can Be Used to Reduce Pathogen Load in Poultry", PLOS One, vol. 7(9), Article e43928, pp. 1-11. (Year: 2012).*
Ramachandran et al., "Oil cakes and their biotechnological applications—A review", Bioresource Technology, vol. 98, pp. 2000-2009. (Year: 2010).*
Lichtenwalner, "Poultry—Nutrition for Chickens", https://web.archive.org/web/20100606151043/https://extension.umaine.edu/livestock/poultry/nutrition-for-chickens (accessed Jun. 23, 2022). (Year: 2007).*
Search Report and Written Opinion dated Jan. 11, 2010 in International Application No. PCT/IB2018/057976, 6 pages.

* cited by examiner

*Primary Examiner* — Michelle F. Paguio Frising
*Assistant Examiner* — Grant C Currens
(74) *Attorney, Agent, or Firm* — C. Rachal Winger; Lee & Hayes PC (57) ABSTRACT

A probiotic composition comprising *Bacillus amyloliquefaciens, Enterococcus faecalis, Lactobacillus salivarius, Lactobacillus johnsonii, Lactobacillus gallinarum* and *Lactobacillus crispatus* is provided. The probiotic composition stimulates the immune response of chickens without negatively affecting growth performance. The probiotic composition can be added to poultry feed to improve the health and performance of chickens, and can be used as a replacement for antibiotic supplementation.

12 Claims, 5 Drawing Sheets

PROBIOTIC COMPOSITION

CROSS-REFERENCE TO RELATED APPLICATIONS

This application is a U.S. National Phase application based on International Patent Application No. PCT/IB2018/057976 filed Oct. 15, 2018, which claims priority from South African provisional patent application number 2017/06932 filed on 13 Oct. 2017, both of which are incorporated by reference herein.

FIELD OF THE INVENTION

This invention relates to a probiotic composition, and in particular to a probiotic composition for poultry.

BACKGROUND TO THE INVENTION

The commercial poultry industry is ranked amongst the highest sources of animal protein. A significant problem in the industry is that despite advances in housing and feeding, bacterial and fungal infections cause substantial financial losses. These infections result in weight loss, poor meat quality and often death. Of all bacterial pathogens, *Salmonella*, *Campylobacter* and *Clostridium* spp. are responsible for most of the infections and, if not controlled, may pose a health risk to other farm animals and humans.

Commercial poultry farmers therefore often use antibiotics as feed additives in order to control bacterial pathogens in their birds. This has led to an increase in the development of antibiotic resistance, and the use of antibiotics in food production has now been banned in some regions, including the United States and Europe. There is also a growing demand from consumers for antibiotic-free food products. As a result, there is a need for an alternative treatment to antibiotics which can improve the health of poultry and other farmed birds and also decrease the proliferation of food-borne pathogens.

Probiotics, prebiotics, synbiotics, enzymes, organic acids and herbs have been considered as alternatives to antibiotics. Probiotics are beneficial health-promoting bacteria which naturally occur in the gastrointestinal tract (GIT), forming a symbiotic relationship with the host. In some animals, they have been shown to protect hosts against pathogen colonisation, improve digestion, increase growth and enhance the immune system.

However, probiotics do not appear to be effective in all animals. Research has shown that the effectiveness of the probiotic bacteria and the health benefits these bacteria generate is often host-specific. For example, bacterial probiotics have been shown to be effective in pigs, cattle and pre-ruminant calves, but there are contradictory results concerning whether the growth performance of poultryis improved by probiotics. This may be due to differences in microbial species, incorrect preparation of the probiotics, poor adherence to the gut wall and mucosa, environmental factors, or poor management.

There is therefore a need for a suitable probiotic for farmed poultry which is able to improve the health or growth of the host and/or reduce contamination of poultry meat.

SUMMARY OF THE INVENTION

According to a first embodiment of the invention, there is provided a probiotic composition comprising *Bacillus amyloliquefaciens*, *Enterococcus faecalis*, *Lactobacillus salivarius*, *Lactobacillus johnsonii*, *Lactobacillus gallinarum* and *Lactobacillus crispatus*.

The probiotic composition may also include other bacteria species, probiotic microorganisms and/or additives.

The probiotic composition may be for administering to poultry, and in particular, to chickens.

The probiotic composition may be formulated for oral administration, for example, in combination with poultry feed.

The probiotic composition may be formulated into a feed additive or supplement.

The probiotic composition may be used for improving the immune system, digestion, growth and/or health or for reducing mortality rates of poultry which feed on the composition. The composition may also be used to inhibit colonisation of pathogenic bacteria, such as *Salmonella enterica*, *Escherichia coli* and *Listeria monocytogenes*, in the meat from the poultry.

The *Bacillus amyloliquefaciens* strain may be the strain designated as DPN123, the *Enterococcus faecalis* strain may be the strain designated as DPN94, the *Lactobacillus salivarius* strain may be the strain designated as DPN181, the *Lactobacillus johnsonii* strain may be the strain designated as DPN184, the *Lactobacillus gallinarum* strain may be the strain designated as DPN164 and/or the *Lactobacillus crispatus* strain may be the strain designated as DPN167.

According to a second embodiment of the invention, there is provided the use of a composition as described above in the manufacture of a prophylactic for preventing an infection in poultry.

According to a third embodiment of the invention, there is provided the use of a composition as described above in the manufacture of a prophylactic for improving the immune system, digestion, growth and/or health of poultry or for reducing mortality rates of poultry.

According to a fourth embodiment of the invention, there is provided the use of a composition as described above in the manufacture of a prophylactic for preventing or reducing the presence of pathogenic bacteria in poultry meat.

According to a fifth embodiment of the invention, there is provided the use of a composition as described above in the manufacture of a medicament for maintaining health of poultry.

According to a sixth embodiment of the invention, there is provided a poultry feed comprising *Bacillus amyloliquefaciens*, *Enterococcus faecalis*, *Lactobacillus salivarius*, *Lactobacillus johnsonii*, *Lactobacillus gallinarum* and *Lactobacillus crispatus*.

According to a seventh embodiment of the invention, there is provided a method of increasing immune responses in poultry, the method comprising administering an effective amount of a probiotic composition as described above to poultry.

The probiotic composition may be administered together with, or as part of, the poultry feed.

The probiotic composition may be administered in the absence of antibiotic supplementation.

The probiotic composition may be administered at about $10^7$ to about $10^9$ CFU per day, for example from about $1 \times 10^8$ to about $4.1 \times 10^8$ CFU of the probiotic per day.

DETAILED DESCRIPTION OF THE INVENTION

A composition comprising *Bacillus amyloliquefaciens*, *Enterococcus faecalis*, *Lactobacillus salivarius*, *Lactobacillus johnsonii*, *Lactobacillus gallinarum* and *Lactobacillus crispatus* is described.

The composition can be administered to poultry birds as a probiotic, such as in combination with or as a supplement or additive to poultry feed. The poultry can be chickens, ducks, geese, turkeys, quails, guinea fowls, pheasants, ostriches or pigeons. In particular, the composition is intended to be administered to chickens (*Gallus gallus domesticus*), and more particularly, to broilers.

The 6 bacteria species can be freeze-dried and combined to yield a total cell count of about $2.8 \times 10^8$ CFU/g probiotic composition. This can comprise about $2.6 \times 10^7$ CFU *L. crispatus*, about $3.6 \times 10^7$ CFU *L. salivarius*, about $1.3 \times 10^8$ CFU *L. gallinarum*, about $1.9 \times 10^7$ CFU *L. johnsonii*, about $5.1 \times 10^7$ CFU *E. faecalis* and about $1.9 \times 10^7$ CFU *B. amyloliquefaciens*. The probiotic composition will typically be administered at about $10^7$ to about $10^9$ CFU per day, for example at from about $1 \times 10^8$ to about $4.1 \times 10^8$ CFU of the probiotic composition per day.

At least some of the bacteria in the composition produce phytase and amylase, which degrade phytic acid and starch, respectively. Production of these enzymes by the bacteria should assist the birds' digestion and utilisation of feed, thereby enhancing their growth.

The bacteria also produce high concentrations of lactic acid and hydrogen peroxide, which have been shown to inhibit the growth of food-borne pathogens such as *Salmonella enterica*, *Escherichia coli* and *Listeria monocytogenes* in vitro. Furthermore, *Bacillus amyloliquefaciens* DPN123 produces an antimicrobial compound that has been shown to be active against Gram-positive and Gram-negative food-borne pathogens in vitro. Bile salt hydrolase is also produced.

Each of the isolated strains shows a high tolerance towards acidic environments and high bile salt concentrations in vitro, suggesting that they have a high probability of surviving the stomach environment and populating the walls of the GIT after oral administration. The strains also possess aggregative abilities, which is an indication of their ability to form biofilms and bind to epithelial cells, thereby possibly preventing adhesion and successful establishment of pathogenic strains in the GIT. The bacterial cells further produce exopolysaccharides (EPS) as protection against environmental stress and which act as prebiotics, conferring additional health benefits to the host.

In one embodiment of the invention, the *B. amyloliquefaciens* is a strain which has been designated DPN123. In the same or a different embodiment of the invention, the *E. faecalis* is a strain which has been designated DPN94. In either of the previous embodiments or a different embodiment of the invention, the *L. salivarius* is a strain which has been designated DPN181. In any of the previous embodiments or a different embodiment of the invention, the *L. johnsonii* is a strain which has been designated DPN184. In any of the previous embodiments or a different embodiment of the invention, the *L. gallinarum* is a strain which has been designated DPN164. In any of the previous embodiments or a different embodiment of the invention, the *L. crispatus* is a strain which has been designated DPN167.

It is envisaged that the bacteria in the composition will line all or a significant portion of the GIT of the birds and confer protection against at least some pathogens, and will also boost the immune system of the birds and/or enhance digestion. Thus, the health of the birds should improve, hopefully leading to an increase in bird mass and a decrease in bird mortalities. This should in turn result in a financial gain for farmers. Meat from the chickens is also less likely to carry food-borne pathogens, thus improving food safety for consumers.

Administering the probiotic composition of the invention to farmed birds will also hopefully assist farmers in successfully rearing the birds without the use of antibiotics.

The invention will now be described in more detail by way of the following non-limiting example.

Selection of Bacteria for an Embodiment of a Multi-Species Probiotic Composition Bacteria from different segments of the gastrointestinal tract (GIT) of 25 healthy free-range broilers were isolated. Probiotic bacteria need to be tolerant towards acidic conditions and bile salts to survive transit in the GIT. The isolated strains were therefore assessed for in vitro tolerance towards simulated gastrointestinal tract conditions. Isolates from each section of the GIT were also screened for probiotic properties such as the production of digestive enzymes (e.g. amylase, phytase and bile salt hydrolase), hydrogen peroxide, exopolysaccharides and antimicrobial compounds, ability to aggregate and form biofilms, and cell hydrophobicity. In addition, identified probiotic strains were screened for the presence of virulence factors.

Strains were screened for bile salt hydrolase (BSH) production according to the method used by Franz et al. (2001). BSH provides strains with resistance to bile salts, and hydrolyses bile salts to form glycine or taurine, and a steroid core. Hydrolysed bile salts compared to non-hydrolysed are less absorbed in the intestine, leaving more free bile acids to be excreted via the faeces. Increased excretions of bile salts decrease the total amount of available bile salts available. Lost bile salts can be replenished via synthesis from cholesterol, which subsequently leads to a reduction in cholesterol serum levels.

Amylase activity was determined using a starch hydrolysis agar plate assay as previously described by Deb et al. (2013). Amylase is capable of hydrolysing $\alpha$-1,4-glycosidic linkages in polysaccharides containing three or more 1,4-$\alpha$-linked glucose units and has specificity towards starches, glycogen and oligosaccharides. Amylase supplementation to feed has been shown to significantly improve digestibility of nutrients and improve broiler growth performance.

Strains producing phytase were determined using an agar plate assay as previously described by Bae et al. (1999). Production of phytases is beneficial as they release energy from anti-nutritive phytic acid, leading to improved broiler growth. In addition, phytases reduce the antinutritional effect of phytic acid, improving the bioavailability of phosphorous, calcium, magnesium, iron and zinc.

Bacteria employ numerous mechanisms to tolerate harsh environmental conditions. This includes surrounding their outer membranes with exopolysaccharides (EPS). In addition, EPS also modulates the microbiome composition by selectively promoting the growth of beneficial bacterial. EPS producers were identified using an agar plate assay as previously described by Stingele et al. (1996).

Isolates producing hydrogen peroxide were identified using an agar plate assay (Müller, 1984; Rabe and Hillier, 2003). Hydrogen peroxide inhibits the growth of pathogens such as *Staphylococcus aureus, Salmonella Typhimurium*, and *Listeria monocytogenes*.

Isolates which produced antimicrobial compounds were identified using the agar-well diffusion assay (Van Staden, 2015). Bacteria which produce antimicrobial compounds can modulate the GIT microbiome composition by preventing colonisation of pathogenic bacteria which induces microbiome dysbiosis.

Virulence factors facilitate colonisation in the GIT, and cytolysin has a dual function as haemolytic toxin and bacteriocin. The presence of cyIA, cyIB and cyIM, geIE, cpd, asp1, cob, cad, EF3314, asa1, efaA and ace in the genome of *Enterococcus* strains was therefore determined by PCR and Southern hybridisation. In addition, gelatinase production was determined by stab inoculating cultures in either MRS or BHI broth (supplemented with 3%, w/v, gelatin) and incubating under aerobic and anaerobic conditions at 37° C. for 5 d. After incubation, cultures were cooled to 4° C. for 5 h, and thereafter inspected for fluidity, indicative of gelatin hydrolysis. Southern hybridisation confirmed the absence of the genes.

The ability of strains to aggregate and form biofilms on glass disks was determined by atomic force microscopy (AFM) and confocal microscopy.

Another characteristic was considered for the selection of the probiotic species is the inhibition of pathogens such as *Clostridium perfringens, Salmonella enterica* and *Campylobacter jejeni*. Infection of poultry with *C. perfringens* may damage the intestinal mucosa (necrotic enteritis), leading to decreased nutrient absorption and subsequently decreased growth performance. It also increases mortality rates, and transmission from poultry to humans leads to food-borne diseases. Infections by *S. enterica* and *C. jejeni* cause diarrhoea, thus decreasing feed intake and subsequently decreasing growth performance, and transmission to humans leads to food-borne diseases such as salmonellosis and campylobacteriosis.

A multi-species probiotic composition was designed to include strains from every section of the gastrointestinal tract (GIT), so as to strive for complete colonisation of the GIT in birds to which the composition is administered. Most commercially available probiotics for broilers contain one or two species, most of which have not been isolated from the GIT of chickens. From the initial 609 bacteria isolated from healthy broilers, 6 strains which tolerated acidic conditions (pH 2 to 3), were resistant to bile salts (0.2 to 2.0% w/v), produced exopolysaccharides and possessed desirable characteristics discussed above were selected for inclusion in the probiotic composition. These strains were DPN184, DPN164, DPN167, DPN164, DPN94 and DPN123:

DPN123 was isolated from the duodenum, and produced extracellular amylase, phytase and antimicrobial lipopeptides (surfactin and iturinA1).

DPN94 was isolated from the jejunum and ileum, and produced phytase and bile salt hydrolase. The genome of DPN94 contained several genes that may encode virulence, but not the production of cytolysin.

DPN184 was isolated from the cecum, and produced hydrogen peroxide.

DPN181 was isolated from the colon, and produced hydrogen peroxide and high levels of lactic acid.

DPN167 was isolated from the crop, proventriculus and ventriculus, and produced hydrogen peroxide and bile salt hydrolase.

DPN164 was isolated from the jejunum and ileum.

The 16S rDNA, recA and gyrB genes of these isolates were amplified and their sequences were compared with those listed in GenBank to assign species identity to the isolates.

Isolate DPN184 was identified as *Lactobacillus johnsonii* (16S rDNA 100% sequence similarity to *L. johnsonii* N6.2, recA gene 98.1% sequence similarity to *L. johnsonii* F19785 and gyrB gene 99.5% similarity to *L. johnsonii* F19785).

Isolate DPN181 was identified as *Lactobacillus salivarius* (16S rDNA 99.7% sequence similarity to *L. salivarius*

JCM1046, recA gene 99.4% sequence similarity to *L. salivarius* UCC118 and gyrB gene 98.1% similarity to *L. salivarius* Ren).

Isolate DPN164 was identified as *Lactobacillus gallinarum* (16S rDNA 99.7% sequence similarity to *L. gallinarum* 126, recA gene 100% sequence similarity to *L. gallinarum* LMG 9435T and gyrB gene 99% similarity to *L. gallinarum* BCRC 17266).

Isolate DPN167 was identified as *Lactobacillus crispatus* (16S rDNA 99.9% sequence similarity to *L. crispatus* ST1, recA gene 99.6% sequence similarity to *L. crispatus* LMG 11415 and gyrB gene 99.7% similarity to *L. crispatus* ST1).

Isolate DPN123 was identified as *Bacillus amyloliquefaciens* (16S rDNA 99.7% sequence similarity to *B. amyloliquefaciens* L-S60, recA gene 99.2% sequence similarity to *B. amyloliquefaciens* BCRC 17266 and gyrB gene 99.7% similarity to *B. amyloliquefaciens* chenj).

Isolate DPN94 was identified as *Enterococcus faecalis* (16S rDNA 99.7% sequence similarity to *E. faecalis* ATCC 29212, recA gene 99.8% sequence similarity to *E. faecalis* ATCC 29212 and gyrB gene 100% similarity to *E. faecalis* DENG1).

Extracellular amylase (which could increase starch degradation, improving growth performance) was thus produced by *Bacillus amyloliquefaciens* DPN123. Hydrogen peroxide (which could assist cells in inhibiting colonisation of sensitive pathogenic bacteria) was produced by *L. johnsonii* DPN184, *L. salivarius* DPN181 and *L. crispatus* DPN167. Phytase enzymes (which could increase nutrient availability in feed, improving growth performance) were produced by *B. amyloliquefaciens* DPN123 and *E. faecalis* DPN94. Antimicrobial lipopeptides surfactin and iturin A1 were produced by *B. amyloliquefaciens* DPN123 and showed antimicrobial activity towards *M. luteus* ATCC 4698, *L. monocytogenes* EDGE, Enteroinvasive *E. coli* ATCC 43892 and *S. enterica* serovar Enteritidis A9. Bile salt hydrolase (which could indirectly lead to lowering of cholesterol effects) was produced by *E. faecalis* DPN94 and *L. crispatus* DPN167. The genome of *E. faecalis* DPN94 encoded for virulence genes cad, ace, slyA, asa1, EF3314, EF0109, cob, asp1, efaA, gelE and cpd, but did not encode for cytolysin (cylA, cylB and cylM).

Assessment of Probiotic Feed Additive

The effects and safety of the multispecies probiotic composition comprising *L. johnsonii* DPN184, *L. salivarius* DPN164, *L. crispatus* DPN167, *L. gallinarum* DPN164, *E. faecalis* DPN94 and *B. amyloliquefaciens* DPN123 as a feed additive in broilers were assessed.

Hatched broilers were randomly divided into three groups with 100 birds per group. The multi-species probiotic was added to the feed of broilers in the first group and its effects on growth performance, size of the lymphoid organs, gizzard mass, mineral content of the tibia bones and red blood cell parameters were assessed on days 19 and 29. The second group of broilers was administered an antibiotic combination of sulphadiazine, colistin and trimethoprim through their feed and subjected to the same tests. The third group of birds received standard feed without additives and served as control.

Preparation of Probiotic Composition

The strains were cultured in molasses medium, which consisted of 5.0% (w/v) molasses, 0.3% (w/v) yeast extract, 0.2% (w/v) peptone, 0.004% (w/v) $MnSO_4$, 0.001% (w/v) Na-citrate, 0.4% (w/v) $K_2HPO_4$ and 0.02% (v/v) Tween80. The medium was sterilised at 121° C. for 15 min, cooled to 25° C., the upper phase removed from the sediment and again autoclaved. Thioglycolate (0.15%, w/v) was added to the growth medium of *L. crispatus* DPN167 and *L. johnsonii* DPN184 to create an anaerobic environment. Incubation was for 3 to 4 days at 37° C. Cells were harvested (8000×g, 10 min, 4° C.), washed with sterile PBS (0.8%, w/v, NaCl; 0.02%, w/v, KCl; 0.142%, w/v, $Na_2HPO_4$; 0.024%, w/v, $KH_2PO_4$; pH 7.5) and resuspended in sterile cryoprotectant (10%, w/v, lactose and 10.0%, w/v, sucrose, autoclaved at 121° C. for 10 min and cooled to 4° C.). The number of viable cells per gram freeze-dried culture was determined by plating onto MRS Agar (Biolab) or BHI Agar (Biolab). Plates were incubated at 37° C. for 24 h under aerobic and anaerobic conditions. The strains were combined to yield a total cell count of $2.8 \times 10^8$ CFU/g freeze-dried powder, consisting of $2.6 \times 10^7$ CFU *L. crispatus* DPN167, $3.6 \times 10^7$ CFU *L. salivarius* DPN181, $1.3 \times 10^8$ CFU *L. gallinarum* DPN164, $1.9 \times 10^7$ CFU *L. johnsonii* DPN184, $5.1 \times 10^7$ CFU *E. faecalis* DPN94 and $1.9 \times 10^7$ CFU *B. amyloliquefaciens* DPN123.

Feeding Trials

The feed contained maize, soya oilcake, sunflower oilcake, canola oilcake, wheat, bran, Ca-phosphate, limestone, salt, lysine, methionine and threonine. The pre-starter was supplied at 178 g per bird (over 7 days). The starter diet was supplied at 354 g per bird (over 7 days), grower diet at 1596 g per bird (over 7 days) and a finisher diet at 1883 g per bird (over 11 days). Feed of broilers from the probiotic treatment group was supplemented with the multi-species probiotic as follows: pre-starter was supplemented with 24 mg dried probiotic cells per gram feed to yield $6.7 \times 10^6$ CFU/gram feed, consisting of $6.1 \times 10^5$ CFU *L. crispatus* DPN167, $8.4 \times 10^5$ CFU *L. salivarius* DPN181, $3.1 \times 10^6$ CFU *L. gallinarum* DPN164, $4.4 \times 10^5$ CFU *L. johnsonii* DPN184, $1.2 \times 10^6$ CFU *E. faecalis* DPN94 and $4.4 \times 10^5$ CFU *B. amyloliquefaciens* DPN123. The starter feed was supplemented with 12 mg probiotic powder per gram feed ($3.3 \times 10^6$ CFU/gram feed, consisting of $3.1 \times 10^5$ CFU *L. crispatus* DPN167, $4.2 \times 10^5$ CFU *L. salivarius* DPN181, $1.6 \times 10^6$ CFU *L. gallinarum* DPN164, $2.2 \times 10^5$ CFU *L. johnsonii* DPN184, $6.1 \times 10^6$ CFU *E. faecalis* DPN94 and $2.2 \times 10^5$ CFU *B. amyloliquefaciens* DPN123). Grower feed was supplemented with 5.4 mg probiotic powder per gram feed ($1.5 \times 10^6$ CFU/gram feed, consisting of $1.4 \times 10^5$ CFU *L. crispatus* DPN167, $1.9 \times 10^5$ CFU *L. salivarius* DPN181, $7.0 \times 10^5$ CFU *L. gallinarum* DPN164, $1.0 \times 10^5$ CFU *L. johnsonii* DPN184, $2.8 \times 10^5$ CFU *E. faecalis* DPN94 and $1.0 \times 10^5$ CFU *B. amyloliquefaciens* DPN123). The finisher was supplemented with 3.5 mg probiotic powder per gram feed ($9.9 \times 10^5$ CFU/g feed, consisting of $9.0 \times 10^4$ CFU *L. crispatus* DPN167, $1.3 \times 10^5$ CFU *L. salivarius* DPN181, $4.4 \times 10^5$ CFU *L. gallinarum* DPN164, $6.2 \times 10^4$ CFU *L. johnsonii* DPN184, $1.8 \times 10^5$ CFU *E. faecalis* DPN94 and $6.5 \times 10^4$ CFU *B. amyloliquefaciens* DPN123). Broilers from the probiotic treatment group received between 1.0 and $4.1 \times 10^8$ CFU daily of the multispecies probiotic consisting of *Lactobacillus crispatus* DPN167 ($9.3 \times 10^6$ to $3.8 \times 10^7$ CFU), *Lactobacillus salivarius* DPN181 ($1.3 \times 10^7$ to $5.3 \times 10^7$ CFU), *Lactobacillus gallinarum* DPN164 ($4.6 \times 10^7$ to $1.9 \times 10^8$ CFU), *Lactobacillus johnsonii* DPN184 ($6.8 \times 10^6$ to $2.8 \times 10^7$ CFU), *Enterococcus faecalis* DPN94 ($1.8 \times 10^7$ to $7.5 \times 10^7$ CFU) and *Bacillus amyloliquefaciens* DPN123 ($6.8 \times 10^6$ to $2.8 \times 10^7$ CFU).

Broilers in the antibiotic treatment group (10 cages) received the same ration in the four feeding cycles, but the feed was supplemented with a combination of sulphadiazine (0.375 ppm/gram feed), colistin (0.128 ppm/gram feed) and trimethoprim (0.075 ppm/gram feed) and contained no probiotics. Broilers from the antibiotic treatment group received on average between 7.5 to 61.1 ppm sulphadiazine, 2.6 to 20.9 ppm colistin and 1.5 to 12.2 ppm trimethoprim daily for 29 days. The three antibiotics were selected as they are often included as feed additives. Broilers in the untreated group (10 cages) served as the control and received feed without antibiotics and probiotics. Lactose and sucrose were added to the feed used in each feeding cycle of the antibiotic and control treatment groups to yield concentrations identical to the feed administered to the probiotic treatment group.

Health and Growth Performance

Visual health and growth performance of the birds were evaluated based on daily feed consumption and changes in body mass. Weekly weight and feed intake per pen were recorded, and individual weights were calculated as an average of the pen weight. Average feed conversion ratio (FCR) calculated from the feed intake (FI) and body weight gain (BWG). All the birds were weighed, and the change in body mass of each cage calculated relevant to the mass recorded on day 1.

Haematology, Organ Weight and Histology

On days 19 and 29, twenty birds per treatment were randomly selected, euthanised by cervical dislocation and blood collected into K2-EDTA tubes by exsanguination. These two days were selected based on the developing stage of the GIT. Previous studies have shown that on day 19 the GIT is not fully developed, whereas 10 days later, on day 29, the GIT is considered mature. The spleen and bursa Fabricius of twenty birds per treatment on days 19 and 29, and the gizzards on day 29 were excised and weighed. The duodenum of 20 broilers per treatment on days 19 and 29 were collected and longitudinally dissected.

In Vivo Inhibition of *L. monocytogenes*

The ability of the antibiotic and probiotic feed additives in inhibiting colonisation and proliferation of *L. monocytogenes* in vivo was assessed. On day 14, twelve broilers per treatment group were each placed in separate cages. Water and feed were supplied ad libitum. On day 15, the feed was withdrawn 2 h before the administration of *L. monocytogenes* EGDe, a bioluminescent strain obtained from Caliper Life Sciences (Massachusetts, USA). Strain EGDe contains plasmid PL2lux with the luxABCDE operon of *Photorhabdus luminescence*. Each of the birds was administered 100 μl (4.28×10$^8$ CFU) *L. monocytogenes* EGDe by intragastric gavage. Broilers from the probiotic treatment group were administered 100 μl of the multi-species probiotic (8.34×10$^8$ CFU) by intragastric gavage, 2 h before the administration of *L. monocytogenes* EGDe.

The probiotic preparation was prepared as follows: *L. crispatus* DPN167, *L. salivarius* DPN181, *L. gallinarum* DPN164, *L. johnsonii* DPN184 and *E. faecalis* DPN94 were cultured in MRS broth for 12 h at 37° C. under anaerobic conditions. *Bacillus amyloliquefaciens* DPN123 was cultured in BHI broth for 12 h at 37° C. under aerobic conditions using an orbital shaker at 100 rpm. Cells were harvested (8000×g, 3 min, 25° C.), washed with two volumes of sterile PBS and resuspended in 100 μl gavage buffer (0.2 M NaHCO$_3$ buffer containing 1%, w/v, glucose, pH 8) to yield 8.3×10$^8$ CFU (5.2×10$^7$ CFU *L. crispatus* DPN167, 6.2×10$^7$ CFU *L. salivarius* DPN181, 1.2×10$^8$ CFU *L. gallinarum* DPN164, 1.3×10$^8$ CFU *L. johnsonii* DPN184, 2.3×10$^8$ CFU *E. faecalis* DPN94 and 2.4×10$^8$ CFU *B. amyloliquefaciens* DPN123). *Listeria monocytogenes* EGDe was cultured in BHI broth (supplemented with 7.5 μg/ml chloramphenicol) under aerobic conditions using an orbital shaker at 100 rpm for 6 h at 37° C. Cells were harvested (8000×g, 3 min, 25° C.), washed with two volumes of sterile PBS and resuspended in gavage buffer to yield 4.2×10$^8$ CFU per 100 μl.

After 2 h, and again 3.5 h, of administering *L. monocytogenes* EGDe, six broilers per treatment group were euthanised by cervical dislocation. The gastrointestinal tract (GIT) of each bird was dissected longitudinally and screened for the emission of bioluminescence from cells of *L. monocytogenes* EGDe by using the Caliper in vivo imaging system (IVIS® 100, Caliper Life Sciences). The IVIS was equipped with a cooled charge-coupled-device camera mounted on a light-tight specimen chamber. Exposure was 3 min. Photons emitted at 620 nm were calculated using the software version 3 of Caliper Life Sciences. The values obtained were expressed as photons per second per cm$^2$ per steradian (p·S$^{-1}$·cm$^{-1}$·sr$^{-1}$). Regions of interest (ROI) were selected manually. Background bioluminescence was corrected for by overlaying images from intestines with non-bioluminescent bacteria. The GIT of each bird was then dissected to separate the duodenum, jejunum, ileum, ceca and colon. Each section was weighed, homogenised in sterile PBS, serially diluted and plated on BHI agar supplemented with 7.5 μg/ml chloramphenicol. Plates were incubated at 37° C. for 24 h and the number of viable cells expressed as CFU/gram gut.

Results and Discussion

Figure 1:
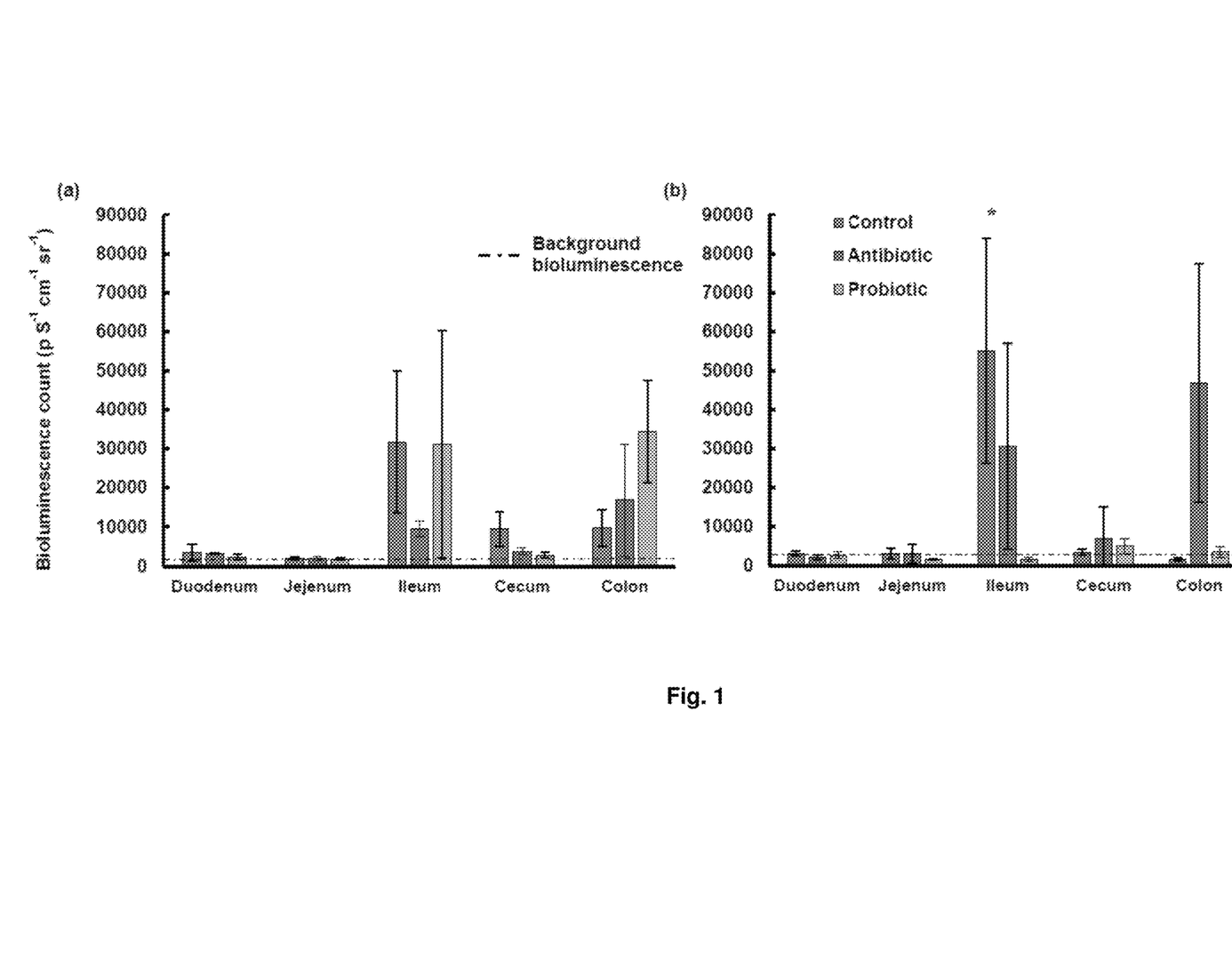
FIG. 1 shows bioluminescence counts (p S-1 cm-1 sr-1) for the different gastrointestinal compartments (duodenum, jejunum, ileum, cecum and colon) of broilers from the different treatment groups (multi-species probiotic, antibiotic combination and control) at (a) 2 and (b) 3.5 h after administration of *L. monocytogenes* EGDe. * Indicates significant differences (p<0.05; Kruskal-Wallis nonparametric test). Error bars indicate standard deviations (n=12).
Figure 2:
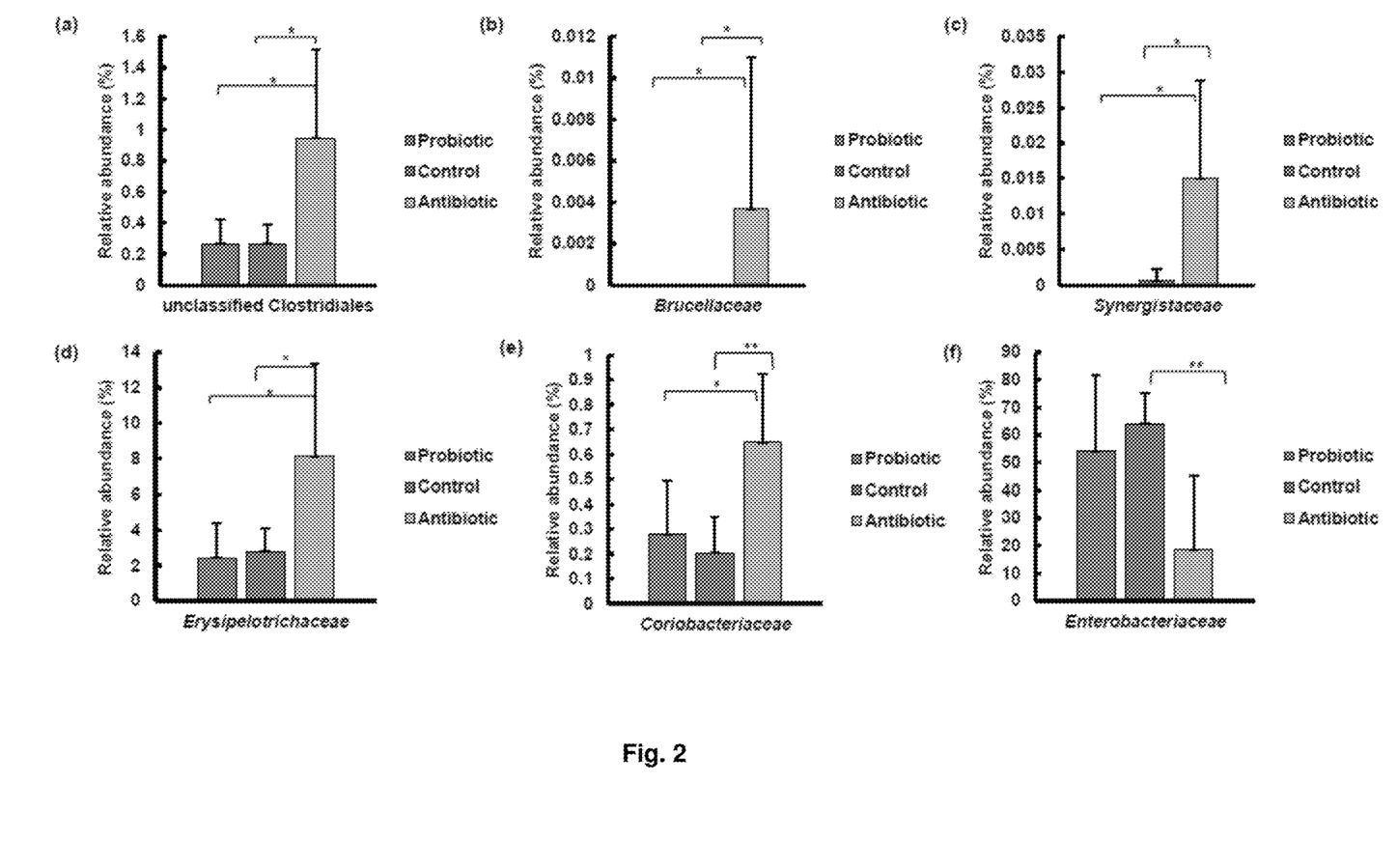
FIG. 2 shows cecal bacterial families, i.e. (a) unclassified Clostridiales, (b) *Brucellaceae*, (c) *Synergistaceae*, (d) *Erysipelotrichaceae*, (e) *Coriobacteriaceae* and (f) *Enterobacteriaceae* whose abundance significantly differs between the different treatments groups' i.e. multi-species probiotic, antibiotic combination and untreated (ANOVA significance, * indicates p<0.05 and **p<0.001). Error bars indicate standard deviations (n=6).

Supplementation of broiler feed with the antibiotic combination or multi-species probiotic had no effect on the weight gain, feed intake, feed conversion ratios, relative lymphoid organ weights, relative gizzard weights, tibia bone parameters and haematological parameters. Broilers from the antibiotic treatment group had higher levels of lymphocytes and basophils counts, and the control group had larger villi area, but these effects were transient and only statistically significant on day 19. Reduced *L. monocytogenes* bioluminescence was observed in the ileum of broilers receiving the multi-species probiotic at 3.5 h after administration of the pathogen, indicating that the probiotic can decrease pathogen metabolic activity (FIG. 1). The microbiome of broilers from the antibiotic treatment group had significant lower levels of *Enterobacteriaceae*, and higher levels of unclassified *Clostridiales, Brucellaceae, Synergistaceae, Erysipelotrichaceae* and *Coriobacteriaceae* in their cecum on day 29 (FIG. 2).

Interaction of Pathogenic and Probiotic Bacteria with Epithelial Cells

The effect of the multi-species probiotic on Caco-2 epithelial cells was studied by monitoring cytotoxicity, adhesion and invasion and effect on claudin-3 tight junctions between the cells. Changes in the proteome of epithelial cells from the ileum of broilers were recorded when exposed to pathogenic and probiotic bacteria, respectively. The pathogenic strain of *Salmonella enterica enteritidis* (strain 147) was cytotoxic and invaded Caco-2 cells. In addition, strain 147 destroyed the claudin-3 tight junctions between Caco-2 cells, resulting in the disruption of the monolayer. Interaction of *S. enteritidis* with broiler epithelial cells led to the up-regulation of lysozyme C and G, cathelicidin 2 and 3, myeloid protein 1, trypsin inhibitor CITI-1, gallinacin-2 and ubiquitin-fold modifier 1, and the down-regulation of glutaredoxin-1, gallicin-7 and vigilin. Up-regulated proteins acted as chemotactic compounds, inhibitors of microbial enzymes, and played critical roles during stress. Down-regulated proteins activated natural killer cells, and regulated apoptosis and antimicrobial defence systems.

Viable cells of *Lactobacillus salivarius* DPN181, *Lactobacillus crispatus* DPN167, *Lactobacillus gallinarum*

Figure 3:
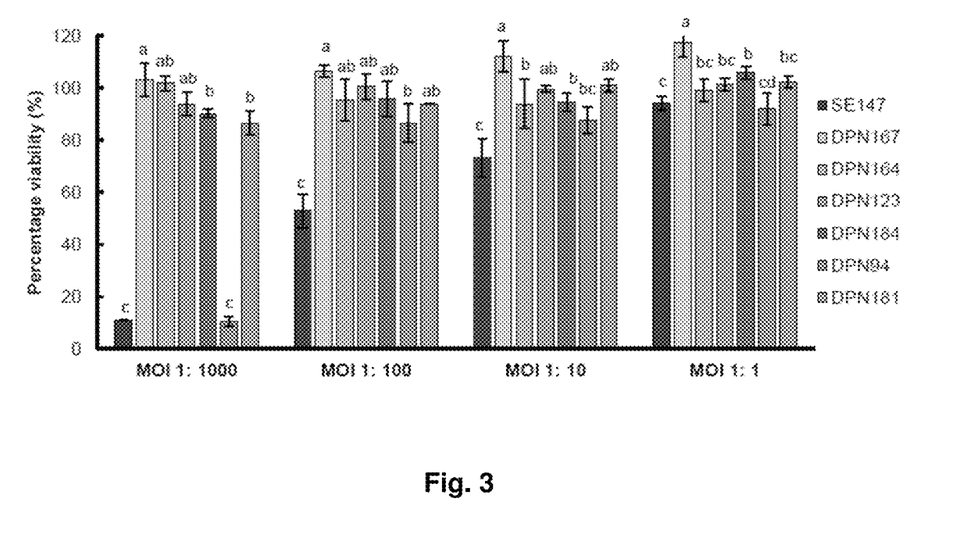
FIG. 3 shows cytotoxicity of bacterial cells towards Caco-2 cells at varying multiplicity of infection (MOI) levels. SE147—*S. enteritidis* 147, DPN167—*L. crispatus*, DPN164—*L. gallinarum*, DPN123—*B. amyloliquefaciens*, DPN184—*L. johnsonii*, DPN94—*E. faecalis* and DPN181—*L. salivarius*. Error bars indicate standard deviations, and bars with different superscripts (a, b, c) differ significantly (p<0.05).

DPN164, *Lactobacillus johnsonii* DPN184, *Enterococcus faecalis* DPN94 and *Bacillus amyloliquefaciens* DPN123, on the other hand, were not cytotoxic to Caco-2 cells (FIG. 3). The probiotic bacteria adhered to Caco-2 cells but did not invade them, and decreased claudin-3 tight junctions but did not disrupt the monolayer. Probiotics decreased claudin-3 tight junctions by producing short-chain fatty acids, hydrogen peroxide and antimicrobial lipopeptides. In broilers administered with the multi-species probiotic, transgelin 2/3, elongation factor-1 beta and anterior gradient 2 were up-regulated, but carnitine O-acetyltransferase, adenylate kinase 2, superoxide dismutase Cu—Zn and protein SET down-regulated. Upregulated proteins were involved in the proliferation, migration and healing of cells and regulation of the cytoskeleton, whereas down-regulated proteins were important in fatty acid transport, energy homeostasis, nucleotide metabolisms, free-radical elimination and signal transduction. Concluded from these studies, the multi-species probiotic was non-toxic and interacted with epithelial cells in a symbiotic manner.

Figure 4:
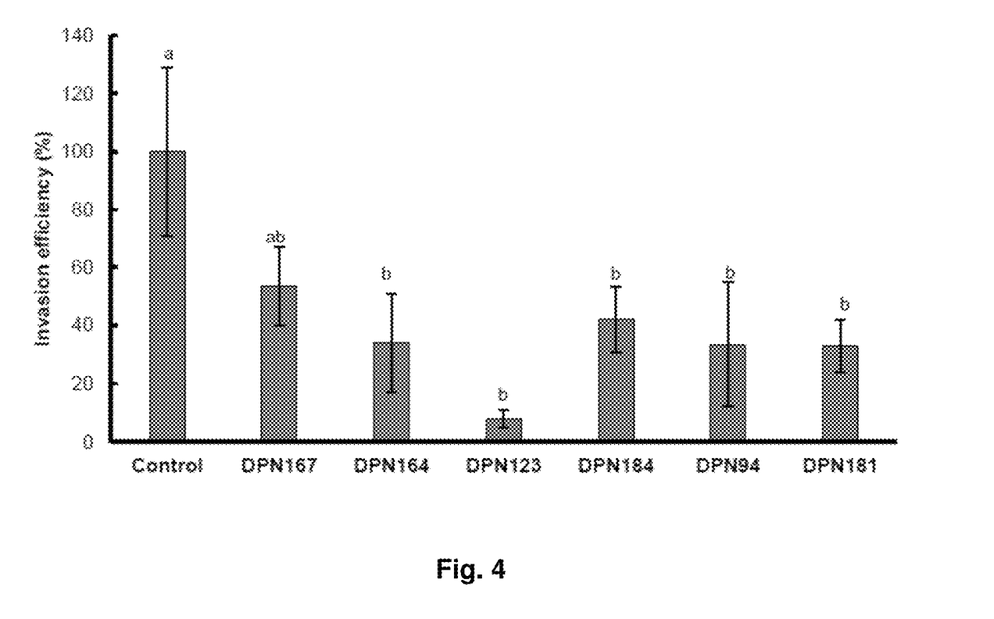
FIG. 4 shows *Salmonella enteritidis* 147 invasion efficacy after exposure to bacterial metabolites originating from control (untreated *S. enteritidis* 147 cells), DPN167—*L. crispatus*, DPN164—*L. gallinarum*, DPN123—*B. amyloliquefaciens*, DPN184—*L. johnsonii*, DPN94—*E. faecalis* and DPN181—*L. salivarius*. Error bars indicate standard deviations, and bars with different superscripts (a, b, c) differ significantly (p<0.05).

Although the multi-species probiotic was not cytotoxic, the metabolic end products were. The ability of probiotic metabolites in inhibiting *S. enteritidis* invasion is shown in FIG. 4. Invasion efficiency of *S. enteritidis* 147 significantly decreased after exposure to metabolites originating from *L. johnsonii* DPN184, *L. salivarius* DPN181, *L. gallinarum* DPN164, *E. faecalis* DPN94 and *B. amyloliquefaciens* DPN123.

Controlling *Salmonella* Colonisation in Broilers with Antibiotic and Probiotic Feed Additive

*Salmonella* is a natural inhabitant of the broiler GIT and rarely cause mortalities, but rather poses a threat as foodborne pathogen for humans. High intestinal cell numbers may lead to contaminated meat and the outbreak of salmonellosis. Various feed additives are therefore used to control cell numbers of *Salmonella* in broilers.

The ability of the multi-species probiotic in inhibiting *Salmonella enterica* subsp. *enterica* serovar *enteritidis* A9 colonisation in comparison to an antibiotic (oxytetracycline) was assessed in vivo. The ability of these treatments in inhibiting *Salmonella* colonisation was assessed by following *Salmonella* colonisation in the cecum, determining the effect on growth performance, haematological parameters, serum bactericidal and lysozyme activity, immune organ weights and T-lymphocyte response rates.

A first group of broilers (119 birds) was administered orally via feed with 2 to $8.9 \times 10^7$ CFU of the multi-species probiotic per day, from day 1, for 29 days. A second group (119 broilers) received orally 4 to 31 mg oxytetracycline per day, over the same period. Broilers in group 3 (119 birds) acted as a positive control (*Salmonella* infected) and those in group 4 (119 birds) acted as a negative control (uninfected). Birds from groups 3 and 4 were not treated with the probiotic or oxytetracycline. On days 9 and 10, broilers in group 1, 2 and 3 were infected with $9 \times 10^7$ CFU of *S. enteritidis* A9. Broilers in group 4 were not infected with *Salmonella*.

Figure 5:
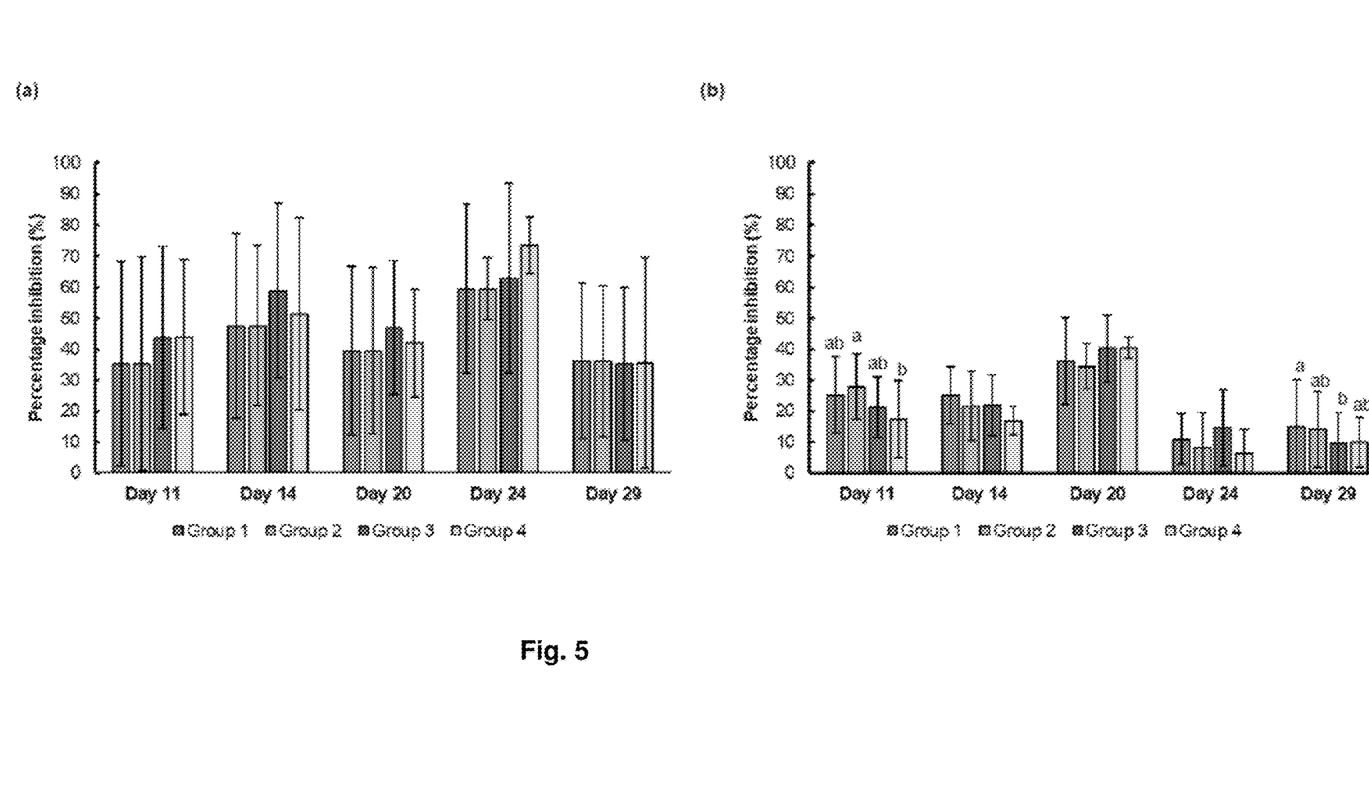
FIG. 5 shows serum bactericidal activity of broilers from the different treatment groups i.e. group 1 (broilers infected with *Salmonella* receiving probiotics as treatment), group 2 (broilers infected with *Salmonella* receiving oxytetracycline as treatment), group 3 (broilers infected with *Salmonella* receiving no treatment) and group 4 (uninfected broilers receiving no treatment) against (a) *E. coli* DH5a and (b) *S. enterica enteritidis* A9 on days 11 (dpi 1), 14 (dpi 4), 20 (dpi 10), 24 (dpi 14) and 29 (dpi 19). Error bars indicate standard deviations, and bars with different superscripts (a, b, c) differ significantly (p<0.05).
Figure 6:
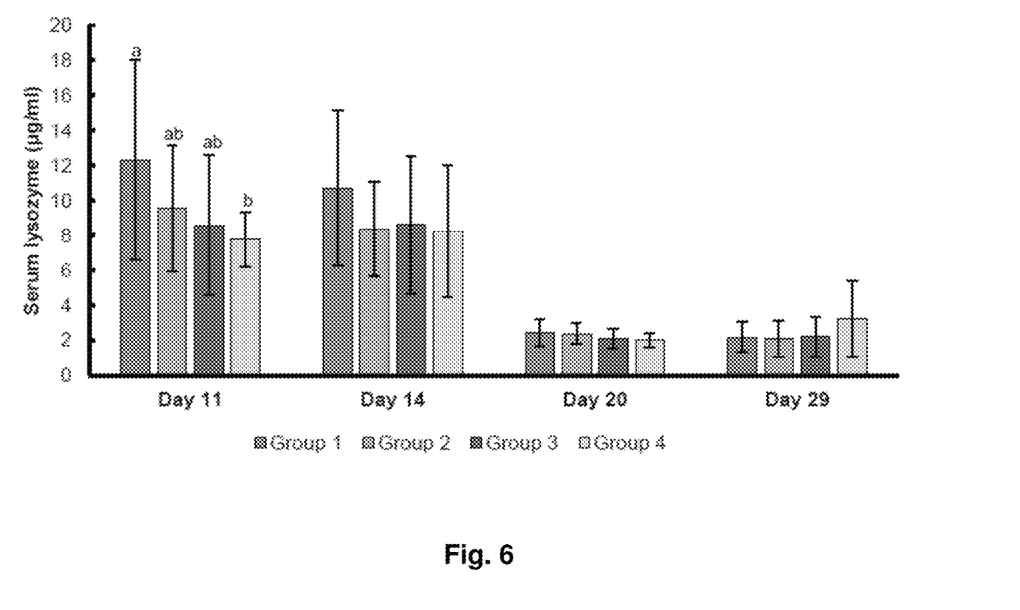
FIG. 6 shows serum lysozyme concentrations of broilers from the different treatment groups i.e. group 1 (broilers infected with *Salmonella* receiving probiotics as treatment), group 2 (broilers infected with *Salmonella* receiving oxytetracycline as treatment), group 3 (broilers infected with *Salmonella* receiving no treatment) and group 4 (uninfected broilers receiving no treatment) on days 11 (dpi 1), 14 (dpi 4), 20 (dpi 10) and 29 (dpi 19). Error bars indicate standard deviations, and bars with different superscripts (a, b, c) differ significantly (p<0.05).
Figure 7:
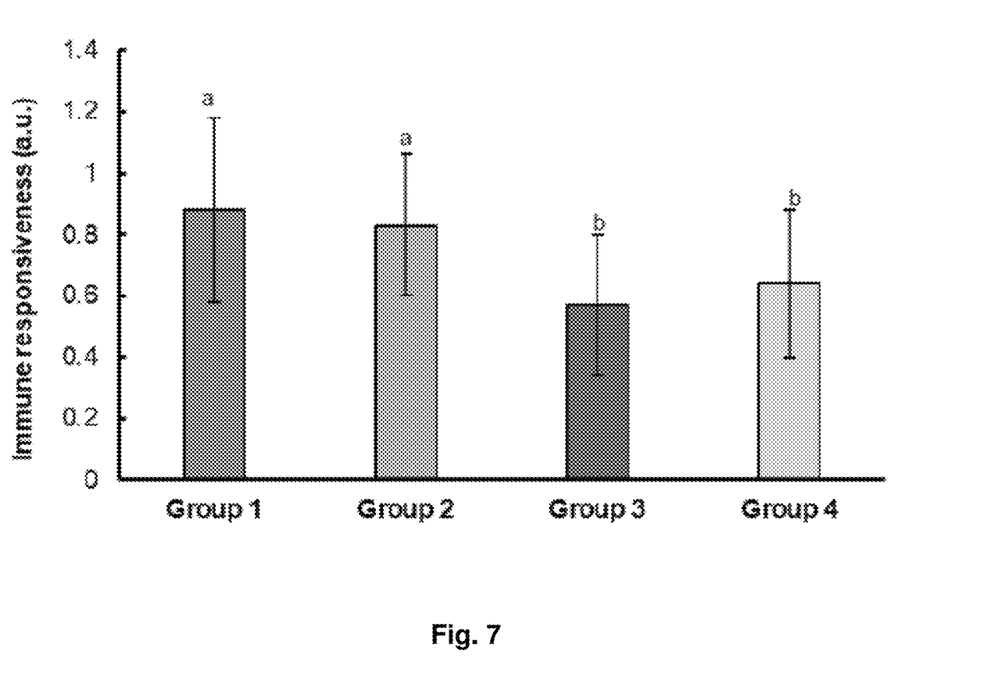
FIG. 7 shows immune T-cell responsiveness of broilers from the different treatment groups i.e. group 1 (broilers infected with *Salmonella* receiving probiotics as treatment), group 2 (broilers infected with *Salmonella* receiving oxytetracycline as treatment), group 3 (broilers infected with *Salmonella* receiving no treatment) and group 4 (uninfected broilers receiving no treatment) on day 17 (dpi 7). Error bars indicate standard deviations, and bars with different superscripts (a, b, c) differ significantly (p<0.05).

Administration of *Salmonella enteritidis* A9 did not alter broiler growth performance, immune organ weights, haematological parameters, serum interferon gamma levels and serum bactericidal activity against *E. coli*. Within the first few days after infection (days 11-14), the faecal cell numbers of *S. enteritidis* A9 of broilers treated with oxytetracycline (group 2) decreased from 7.954 to 0.857 (Log CFU) and remained at this level for 4 days. However, cell numbers increased from day 19 onwards to levels equivalent to those recorded for broilers from the probiotic and positive control treatment groups (groups 1 and 3, respectively). The increase in cell numbers may be due to antibiotics disturbing the microbiome in the GIT, indirectly favouring the colonisation of *Salmonella*. Broilers that received the multi-species probiotic (group 1) had similar levels of *Salmonella* in their cecum as untreated infected broilers (group 3). However, the viable cell numbers of *Salmonella* decreased on day 29 to levels recorded in uninfected broilers (group 4). Treatment with the multi-species probiotic and oxytetracycline increased serum *Salmonella* bactericidal activity and T lymphocyte responses in broilers infected with *Salmonella* (FIG. 5). In addition, probiotic use increased serum lysozyme levels (FIG. 6). Thus, it was concluded that antibiotic and probiotic feed additives increased broiler immune responses in response to *Salmonella* infection (FIG. 7).

The multi-species probiotic composition compares well with benefits reported of commercial probiotics PoultryStar™ from Biomin (*E. faecium, P. acidilactici, B. animalis, L. salivarius,* and *L. reuteri* and prebiotic fructooligosaccharides), CLOSTAT™ from Kemin Industries (*B. subtilis*) and FloraMax™ from Novozymes (*L. salivarius* and *P. parvulus*).

The designed multi-species probiotic possessed numerous beneficial characteristics and its daily use as a feed additive was deemed safe, as probiotic use did not negatively affect the performance of healthy birds. The probiotic strains adhered to intestinal epithelial cells and crosstalk between these cells did not induce negative proteomic changes. The multi-species probiotic also increased broiler immune responses during *Salmonella* infection, which suggests that the strains may be used as an alternative feed additive to improve broiler health and performance.

The above description is by way of example only and it should be appreciated that various modifications may be made to the composition without departing from the scope of the invention. It should, for example, be immediately apparent that the composition is not limited to the specific bacterial strains mentioned in the example, but may include other bacterial strains of the same species with the same or similar characteristics. The probiotic composition may also include additional components, additives and excipients.

Throughout the specification unless the contents requires otherwise, the word 'comprise' or variations such as 'comprises' or 'comprising' should be understood to imply the inclusion of a stated integer or group of integers but not the exclusion of any other integer or group of integers.

REFERENCES

Bae, H. D., Yanke, L. J., Cheng, K. J., Selinger, L. B. (1999). A novel staining method for detecting phytase activity. *J. Microbiol. Methods* 39(1), p 17-22, DOI: 10.1016/S0167-7012(99)00096-2.

Deb, P., Talukdar, S. A., Mohsina, K., Sarker, P. K., Sayen, S. M. A. (2013). Production and partial characterization of extracellular amylase enzyme from *Bacillus amyloliquefaciens* P-001. *SpringerPlus* 2(154), p 1-12, DOI: 10.1186/2193-1801-2-154.

Franz, C. M., Specht, I., Haberer, P., Holzapfel, W. H. (2001). Bile salt hydrolase activity of Enterococci isolated from food: screening and quantitative determination. *J. Food. Prot.* 64(5), p 725-729, DOI; 10.4315/0362-028X-64.5.725.

Müller, H. E. (1984). ABTS peroxidase medium as a highly sensitive plate assay for detection of hydrogen peroxide production in bacteria. *J. Microbiological Methods* 2(2), p 101-102, DOI: 10.1016/0167-7012(84)90035-6.

Rabe, L. K., Hillier, S. L. (2003). Optimization of media for detection of hydrogen peroxide production by *Lactobacillus* species. *J. Clin. Microbiol.* 41(7), p 3260-3264, DOI: 10.1128/JCM.41.7.3260-3264.2003.

Van Staden, A. D. (2015). In vitro and in vivo characterization of amyloliquecidin, a novel two-component Iantibiotic produced by *Bacillus amyloliquefaciens*. PhD Microbiology, Stellenbosch University, Stellenbosch, South Africa.

What is claimed is:

1. A poultry feed comprising maize and a probiotic composition which enhances an immune response in chickens, wherein the probiotic composition consists of (i) freeze-dried bacterial cells from *Bacillus amyloliquefaciens, Enterococcus faecalis, Lactobacillus salivarius, Lactobacillus johnsonii, Lactobacillus gallinarum* and *Lactobacillus crispatus* and (ii) a cryoprotectant.

2. The poultry feed of claim 1, further comprising soya oilcake, sunflower oilcake, canola oilcake, wheat, bran, calcium-phosphate, limestone, salt, lysine, methionine and/or threonine.

3. The poultry feed of claim 1, comprising 24 mg of the dried bacterial cells per gram of the poultry feed, 12 mg of the dried bacterial cells per gram of the poultry feed, 5.4 mg of the dried bacterial cells per gram of the poultry feed, or 3.5 mg of the dried bacterial cells per gram of the poultry feed.

4. A probiotic composition consisting of (i) a mixture of freeze-dried bacterial cells from *Bacillus (B.) amyloliquefaciens, Enterococcus (E.) faecalis, Lactobacillus (L.) salivarius, Lactobacillus (L.) johnsonii, Lactobacillus (L.) gallinarum* and *Lactobacillus (L.) crispatus* and (ii) a cryoprotectant, wherein the probiotic composition enhances an immune response in chickens.

5. The probiotic composition of claim 4, comprising about $1.9 \times 10^7$ CFU/g *B. amyloliquefaciens*, about $5.1 \times 10^7$ CFU/g *E. faecalis*, about $3.6 \times 10^7$ CFU/g *L. salivarius*, about $1.9 \times 10^7$ CFU/g *L. johnsonii*, about $1.3 \times 10^8$ CFU/g *L. gallinarum*, and about $2.6 \times 10^7$ CFU/g *L. crispatus*.

6. The probiotic composition according to claim 4, which is for administering to chickens.

7. The probiotic composition according to claim 4, which is in a form for oral administration.

8. The probiotic composition according to claim 4, which is a feed additive or supplement.

9. The probiotic composition according to claim 4, which is for use in improving the immune system, digestion, growth and/or health or for reducing mortality rates of poultry to which the probiotic composition is administered.

10. The probiotic composition according to claim 4, wherein the mixture of dried bacterial cells are freeze-dried to yield a total cell count of about $2.8 \times 10^8$ colony forming units (CFU)/gram (g).

11. The probiotic composition according to claim 4, wherein the freeze-dried bacterial cells have been harvested from strains of *B. amyloliquefaciens, E. faecalis, L. salivarius, L. johnsonii, L. gallinarum* and L. crispatus isolated from the gastrointestinal tract (GIT) of chickens and which:
   are tolerant to a pH of 2-3;
   are resistant to bile salts;
   produce exopolysaccharides;
   bind to epithelial cells; and
   form biofilms.

12. The probiotic composition according to claim 10, wherein the total cell count of $2.8 \times 10^8$ CFU/g has about $1.9 \times 10^7$ CFU/g *B. amyloliquefaciens*, about $5.1 \times 10^7$ CFU/g *E. faecalis*, about $3.6 \times 10^7$ CFU/g *L. salivarius*, about $1.9 \times 10^7$ CFU/g *L. johnsonii*, about $1.3 \times 10^8$ CFU/g *L. gallinarum*, and about $2.6 \times 10^7$ CFU/g *L. crispatus*.

* * * * *